(12) United States Patent
Rosemeyer et al.

(10) Patent No.: US 9,737,613 B2
(45) Date of Patent: Aug. 22, 2017

(54) COLLOID BONDED MEDICINAL COMPOUNDS

(71) Applicant: B. Braun Melsungen AG, Melsungen (DE)

(72) Inventors: Helmut Rosemeyer, Osnabrück (DE); Edith Malecki, Bad Zwischenahn (DE)

(73) Assignee: B. Braun Melsungen AG, Melsungen (DE)

( * ) Notice: Subject to any disclaimer, the term of this patent is extended or adjusted under 35 U.S.C. 154(b) by 330 days.

(21) Appl. No.: 14/413,716

(22) PCT Filed: Sep. 25, 2013

(86) PCT No.: PCT/EP2013/069979
§ 371 (c)(1),
(2) Date: Jan. 9, 2015

(87) PCT Pub. No.: WO2014/048996
PCT Pub. Date: Apr. 3, 2014

(65) Prior Publication Data
US 2015/0202307 A1 Jul. 23, 2015

(30) Foreign Application Priority Data
Sep. 28, 2012 (EP) .................... 12186555

(51) Int. Cl.
| | | |
|---|---|---|
| A61K 31/70 | (2006.01) | |
| A01N 43/04 | (2006.01) | |
| A61K 47/48 | (2006.01) | |
| C07H 19/06 | (2006.01) | |

(52) U.S. Cl.
CPC ......... *A61K 47/4823* (2013.01); *C07H 19/06* (2013.01)

(58) Field of Classification Search
None
See application file for complete search history.

(56) References Cited

U.S. PATENT DOCUMENTS

| | | | |
|---|---|---|---|
| 7,816,516 B2 | 10/2010 | Sommermeyer et al. | |
| 7,893,226 B2 | 2/2011 | Yedgar | |
| 2005/0063943 A1* | 3/2005 | Sommermeyer | A61K 47/48284 424/85.1 |
| 2005/0118199 A1 | 6/2005 | Esser et al. | |

OTHER PUBLICATIONS

Abstract of European Patent—EP1230935, Aug. 14, 2002, 1 page.
Article—Andronova et al., "Antiviral Activity of Some 2'-Deoxyuridine 5-Arylethynl Derivatives," *Russian Journal of Bioorganic Chemistry*, vol. 29, No. 3, 2003, pp. 262-266.
Article—Beaucage et al., "Deoxynucleoside Phosphoramidites—A New Class of Key Intermediates for Deoxypolynucleotide Synthesis," *Tetrahedron Letters*, vol. 22, No. 20, 1981, pp. 1859-1862.
Article—Kanetsuna et al., "Chemical Analysis of a Mycolic Acid—Arabinogalactan-Mucopeptide Complex of Mycobacterial Cell Wall," *Biochim. Biophys. Acta*, 208, 1970, pp. 434-443.
Article—Luo et al., "A novel 5-fluorouracil prodrug using hydroxyethyl starch as a macromolecular carrier for sustained release," *Carbohydrate Polymers*, 87, 2012, pp. 2642-2647.
Article—Malecki et al., "O-2',3'-Ketal-Nucleolipids of the Cytostatic 5-Fluorouridine: Synthesis Lipophilicity, and Acidic Stability," *Helvetica Chimica Acta*, vol. 93, 2010, pp. 1500-1512.
Article—Nielsen et al., "Application of 2-cyanoethyl N,N,N',N'-tetraisopropylphosphorodiamidite for in situ preparation of deoxyribonucleoside phosphoramidites and their use in polymer-supported synthesis of oligodeoxyribonucleotides," *Nucleic Acids Research*, vol. 14, No. 18, 1986, pp. 7391-7403.
Article—Nielsen et al., "Polymer-Supported Synthesis of Deoxyoligonucleotides Using In-Situ Prepared Deoxynucleoside 2-Cyanoethyl Phosphoramidites," *Recl. Trav. Chim. Pays-Bas.*, vol. 105, 1986, pp. 33-34.
International Search Report for PCT/EP2013/069979 dated Nov. 14, 2013, 3 pages.

* cited by examiner

*Primary Examiner* — Patrick Lewis
(74) *Attorney, Agent, or Firm* — Dority & Manning, P.A.

(57) ABSTRACT

The invention relates to colloids bound medicinal compounds or fluorescent markers, to a process for the preparation thereof, and to a pharmaceutical formulation containing such compounds.

17 Claims, 3 Drawing Sheets

COLLOID BONDED MEDICINAL COMPOUNDS

CROSS REFERENCE TO RELATED APPLICATIONS

Figure 1:
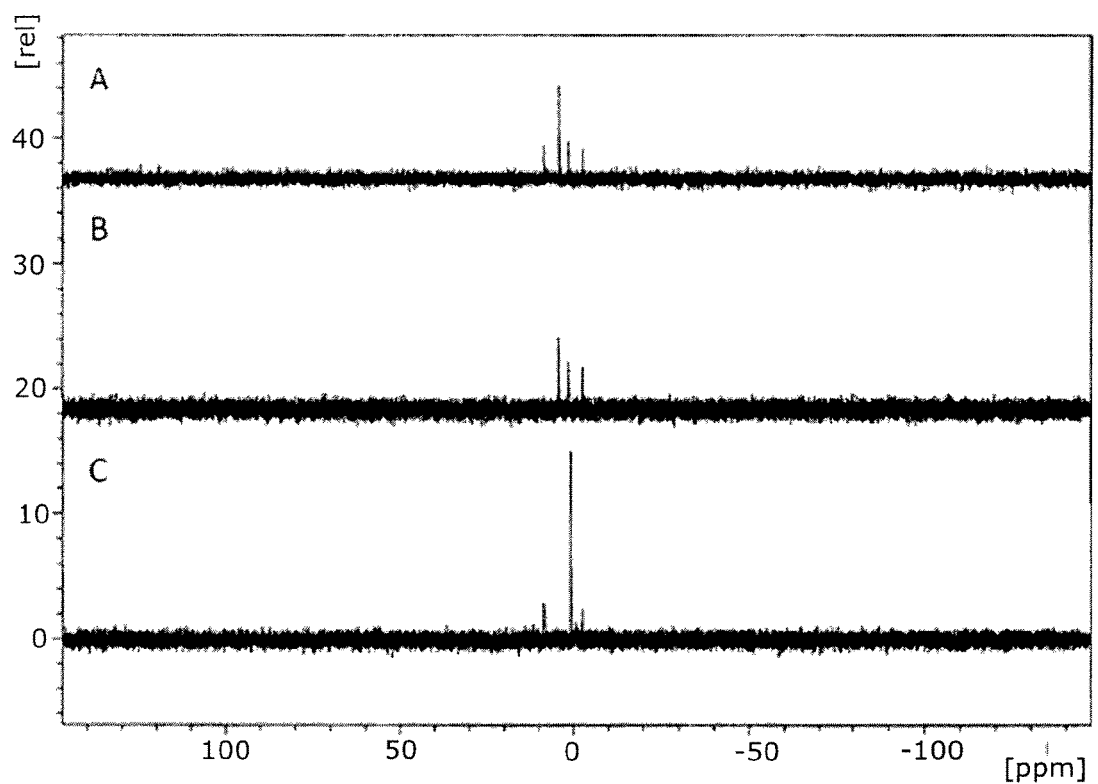
Figure 2:
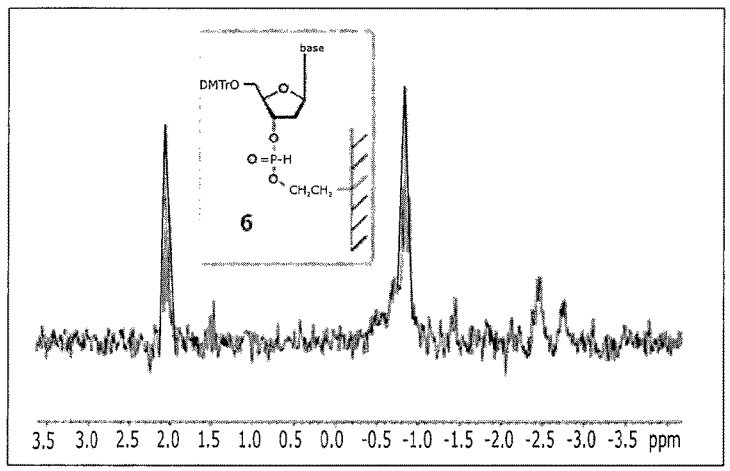

This application is the national stage entry of International Patent Application No. PCT/EP2013/069979 having a filing date of Sep. 25, 2013, which claims priority to and the benefit of European Patent Application No. 12186555.4 filed in the European Patent Office on Sep. 28, 2012, the entire contents of which are incorporated herein by reference.

The invention relates to colloid bound medicinal compounds or fluorescent markers, to a process for the preparation thereof, and to a pharmaceutical formulation containing such compounds.

Achieving good solubility and/or chemical and metabolic stability can be a challenging issue in drug development. As a result, a significant number of drugs or drug candidates exhibit sub-optimal properties, potentially resulting in repeated administration, high doses and associated cost of goods, and represent a burden, both to the patient and the drug companies developing them. Over the last 30 years, a few innovative approaches have been developed to try to address these issues either via formulation strategies and/or bioconjugation methodologies such as PEGylation. Starch derivatives (eg HES) are water soluble semi-synthetic polysaccharides that have been used in large amounts for decades in hospital care notably for the treatment of hypovolemia and that exhibit low toxicology potential. Their behavior in the human body is therefore very well understood. It has recently been reported that they could also be used as biopolymer conjugates and could represent as such an elegant alternative to other methodologies described above.

The covalent binding to colloids enables substances to be introduced by phagocytosis into cells of the immune system, which would not be taken up, or if so only in negligible amounts, without such modification. EP 1 230 935 A1 describes the chemical binding of medicinally active substances to a polysaccharide to form a linker. The uptake of substances by correspondingly specialized cells of the reticulohistiocytic system has been demonstrated for a wide variety of colloids and particles. However, there is still a need to improve the binding complexes in terms of sufficient availability of the medicinally active substance and/or the fluorescence marker at the cells which also requires effective enzymatic cleavage of the medicinally active substance and/or the fluorescence marker from the colloid active substance.

US 2005/0063943 A1 describes the coupling of HES to an oligonucleotide via a peptide bond, starting from amino-functionalized HES.

In "Chemical analysis of a mycolic acid-arabinogalctan-mucopeptide complex of mycobacterial cell wall", Biochemica et Biophysica Acta—General subjects, Elsevier Science Publishers, NL, vol. 208, no. 3, 16. June 1970, pages 434-443 by F. Kanetsuna et al, the authors describe the coupling of a sugar to a polypeptide via a peptide bond. The organo phosphate is present as part of a natural product.

US 2008/0194806 A1 describes the coupling of a lipid or phosphorlipid to a glycosaminoglycan via an amide or ester bond.

US 2005/0118199 A1 discloses a method for covalently bonding a polysaccharide and a microsphere or biomolecule under employment of 4-(4,6-dimethoxy[1,3,5]triazin-2-yl)-4-methyl-morpholinium chloride (DMTMM).

In "A novel 5-fluorouracil prodrug using hydroxyethyl starch as a macromolecular carrier for sustained release", Carbohydrate Polymers, Elsevier Science Publishers, GB, vol. 87, 13. November 2011, pages 2642-2647 by Q. Luo et al, the authors describe the synthesis of 5-fluorouracil coupled HES, starting from the respective nucleobase, via an ester group.

However, none of the above describes the direct covalent coupling of a phosphoramidite to a biomolecule without the use of an amide, ester or peptide bond.

For the introduction of medicinally active substances or fluorescence marker into specific organs and cell systems of the body, the following conditions must be met:
1. The medicament complex, which consists of the medicament chemically bonded to a colloid, should be water-soluble and circulate in the blood for a sufficient period of time.
2. The medicament complex should have no influence on blood clotting.
3. The medicinally active substance must be cleavable from the colloid active substance, especially enzymatically cleavable.

The object of the present invention is to provide a novel and versatile way to link colloids, especially HES molecules or derivatives, to an active ingredient or a fluorescence marker via a phosphor acid diester linkage therefore giving access to novel bioconjugates. These bioconjugates retain biological activity while exhibiting improved drug properties.

Surprisingly, it has now been found that bonding of a medicinally active substance or a fluorescence marker to a colloid (colloid-active compound) via a phosphor acid diester solves the above mentioned problems and serves, in particular, as a suitable transport system for medicaments and/or fluorescence markers covalently linked thereto.

The present invention relates to a compound of general formula (I)

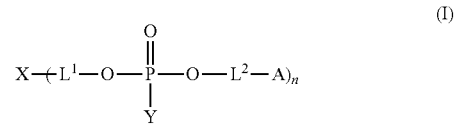

wherein
X is a colloid-active compound;
$L^1$ is a first linker by means of which X and the phosphate group are covalently linked together and wherein $L^1$ is selected from the group consisting of a single bond, alkendiyl, alkendiyl and alkyndiyl;
$L^2$ is a second linker by means of which the phosphate group and A are covalently linked together;
A is a medicinally active substance selected from the group consisting of antibiotics, chemotherapeutics, cytostatic agents, antigens, oligonucleotides, mediators, false metabolic substrates, analgetics and cytotoxic substances; or a fluorescence marker;
Y is either H or OH; and
n is an integer of at least 1.

In a preferred embodiment of the present invention, n is an integer of from 1 to 10,000, preferably from 2 to 1000, more preferably from 5 to 500, especially from 10 to 100.

In a further preferred embodiment the colloid-active compound X is selected from the group consisting of amyloses, amylopectins, acemannans, arabinogalactans, galactomannans, galactoglucomannans, xanthans, carrageenan, hyaluronic acid, deacetylated hyaluronic acid, chitosan, starch and modified starch.

The modified starch is preferably selected from the group consisting of hydroxyalkyl starches, esterified starches, carboxyalkyl starches, hydroxyalkyl carboxyalkyl starch, aminated hydroxyalkyl starch, aminated hydroxyalkyl carboxyalkyl starch and aminated carboxyalkyl starch.

According to an especially preferred embodiment the modified starch is selected from hydroxyethyl starch or aminated hydroxyethyl starch. Preferably the degree of substitution, DS, of the modified starch, especially hydroxyethyl starch, is from 0.2 to 0.8, preferably from 0.3 to 0.6.

Advantageously, the colloid-active compound has an average molecular weight of from 20,000 to 800,000 daltons, preferably from 25,000 to 500,000 daltons, especially from 30,000 to 200,000 daltons.

A in formula (I) is preferably selected from the group consisting of 5-Fluorouracil, Amphotericin B, Daunorubicin, Doxorubicin, Cladribine, Zosyn (Tazosyn), Floxuridine, Delafloxacin, Gemcitabine, Irinotecan, Vadimezan, Fluconazole, Voriconazole and Ravuconazole.

Specifically said medicinally active compound A is selected from formula (II) to (IV)

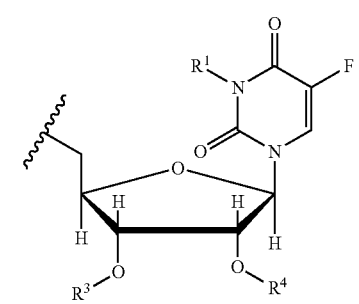

(II)

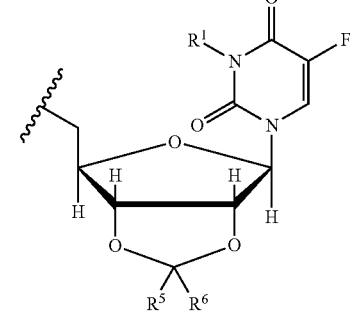

(III)

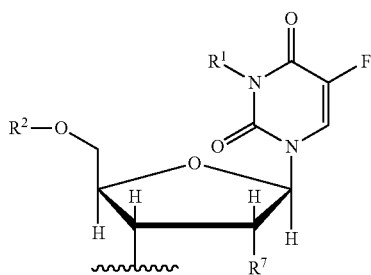

(IV)

wherein
$R^1$ is H or an organic moiety, preferably a $C_1$-$C_{28}$ chain which may be branched or linear and which may be saturated or unsaturated and which may optionally be interrupted and/or substituted by one or more hetero atom(s) (Het1) and/or functional group(s)(G1); or $R^1$ is a $C_3$-$C_{28}$ moiety which comprises at least one cyclic structure and which may be saturated or unsaturated and which may optionally be interrupted and/or substituted by one or more hetero atom(s) (Het1) and functional group(s) (G1);
$R^2$ is H or an organic moiety comprising 1 to 30 carbon atoms;
$R^3$ and $R^4$ represent independently from each other H or a $C_1$-$C_{28}$-alkyl moiety which may optionally be substituted or interrupted by one or more heteroatom(s) and/or functional group(s); or
$R^3$ and $R^4$ form a ring having at least 5 members, preferably a ring having 5 to 8 carbon atoms and wherein the ring may be substituted or interrupted by one or more hetero atom(s) and/or functional group(s);
$R^5$ and $R^6$ represent independently from each other H or a $C_1$-$C_{28}$-alkyl moiety which may optionally be substituted or interrupted by one or more heteroatom(s) and/or functional group(s);
or
$R^5$ and $R^6$ form a ring having at least 5 members, preferably a ring having 5 to 18 carbon atoms and wherein the ring may be substituted or interrupted by one or more hetero atom(s) and/or functional group(s);
$R^7$ is a hydrogen atom or —O—$R^8$;
$R^8$ is H or $C_1$-$C_{28}$ chain which may be branched or linear and which may be saturated or unsaturated and which may optionally be interrupted and/or substituted by one or more hetero atom(s) (Het1) and/or functional group(s) (G1).

In a preferred embodiment substituent $R^1$ is a linear or branched chain comprising 1 to 50 carbon which may be interrupted and/or substituted by one or more hetero atom(s) (Het1) and/or functional group(s)(G1). Preferably, $R^1$ is a linear or branched chain comprising 2 to 40, more preferably 3 to 30, especially 4 to 28 or 6 to 20 or 8 to 16 carbon atoms. In one aspect of the invention $R^1$ is a linear or branched $C_1$-$C_{28}$-alkyl, preferably $C_2$-$C_{20}$-alkyl, more preferably $C_4$-$C_{20}$-alkyl or $C_6$-$C_{18}$-alkyl, especially $C_8$-$C_{16}$-alkyl which may be substituted or unsubstituted. In a further aspect of the invention the carbon chain is interrupted by one or more hetero atom(s) (Het1) wherein the Het1 is preferably selected from O, S and N, more preferably selected from 0 or N. In one aspect the substituent $R^1$ is interrupted by up to 3 hetero atom(s) (Het1), preferably 1 or 2 hetero atoms such as O. In a further aspect of the invention the carbon chain of substituent $R^1$ is interrupted by nitrogen which preferably further branches the chain. An exemplary embodiment of this type of substituent is reflected in the following formula:

wherein $R^9$ and $R^{10}$ are independently selected from a $C_1$ to $C_{30}$ chain which can be saturated or unsaturated, preferably a $C_1$ to $C_{30}$ alkyl, preferably $C_4$ to $C_{24}$ alkyl, more preferably $C_8$ to $C_{22}$ alkyl and especially $C_{12}$ to $C_{18}$ alkyl; or a $C_2$ to $C_{30}$ chain having one or more carbon-carbon double and/or carbon-carbon triple bond(s); and "a" is an integer ranging from 1 to 20, preferably 2 to 18, more preferably 3 to 12 or 4 to 8. However, the linking moiety which links the nitrogen atom with substituents $R^9$ and $R^{10}$ to the 5-fluorouracil moiety can also be a unsaturated carbon chain having 2 to 20 carbon atoms and one or more carbon-carbon double and or carbon-carbon triple bonds. The exemplary substituent of the following formula:

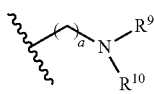

can be synthesized by various synthetic routes. Scheme 1 shows several synthetic routes for precursors which can be attached to the 5-fluorouracil moiety.

In a further reaction the dioctadecylamine can be alkylated with 1,4-dichlorobut-2-yne in the presence of $Na_2CO_3$ in benzene.

In the following Scheme 2 various synthetic routes to obtain single chain precursor or double chain precursor with different chains for the substitution of the 5-fluorouracil moiety are disclosed. The single chain precursor reflected in Scheme 2 is interrupted by a hetero atom (N) or a functional group (amid; NHCO).

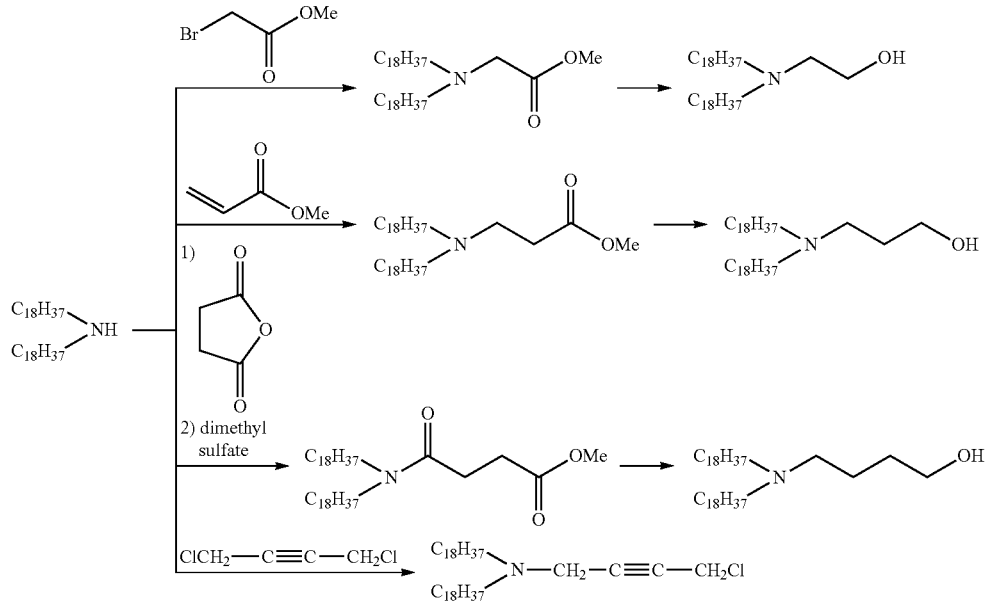

As can be seen from Scheme 1 various precursors for the connection with the nitrogen atom of the 5-fluorouracil moiety can be obtained by different synthetic routes. In a preferred embodiment of the present invention substituent $R^1$ is a double chained substituent. The double chained substituents can be obtained as reflected in Scheme 2.

In a first aspect the dioctadecylamine is reacted with methyl bromoacetate in the presence of dibenzo-[18]-crown-6 which leads to the pure methyl ester in almost quantitative yield. The ester can be reduced with $LiAlH_4$ to give the alcohole.

In order to extend the spacer between the hydroxyl group and the nitrogen carrying the carbon chains the dioctadecylamine can be reacted with methyl acrylate which results in almost quantitative yield to the ester which was further reduced with $LiAlH_4$ to give a lipophilic aminopropanol derivative.

In a further aspect the dioctadecylamine was reacted with succinic anhydride to give the acid which can be converted to the methyl ester by reaction with dimethyl sulphate in the presence of $K_2CO_3$. The methyl ester can then be reduced with $LiAlH_4$ yielding the further extended alcohole, namely a lipophilized 4-aminobutanol derivative.

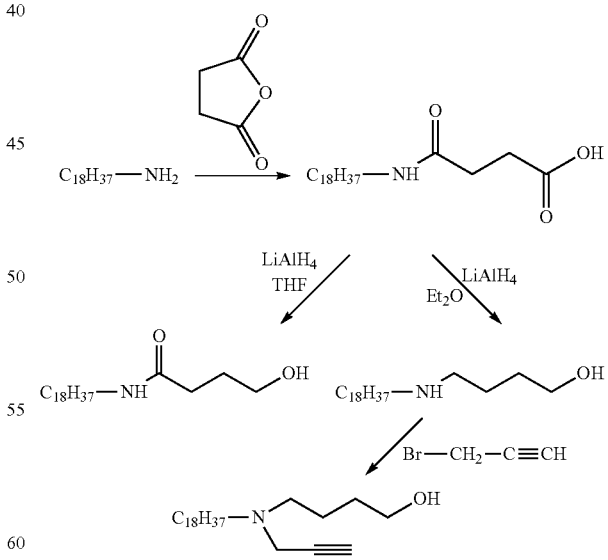

As can be seen from Scheme 2 lipid single chain precursors can be obtained by the reaction of octadecylamine with succinic anhydride which leads to the acid which can be reduced with $LiAlH_4$ in THF at ambient temperature which leads to the reduction of the carboxylic group only, but not of the amide moiety and results into the amido alcohole in 82% yield. Replacement of THF by $Et_2O$ however results in the amino alcohol in a high yield of 84%. Subsequent reaction of amino alcohol with propargyl bromide results in the double chained alkine in 61% yield.

It has surprisingly been found that the lipophilic carbon chains comprising a hydroxyl functional group or a halide can be introduced regioselectively into the 5-fluorouracil derivative. The lipophilic groups can principally be positioned either at the heterocyclic base or at the glyconic moiety and can be introduced by various methods, e.g. by base-catalysed alkylation with alkyl halides.

The reaction of unprotected 5-fluorouracil derivatives with halogenated alkyls, alkenes or alkynes can be performed in $DMF/K_2CO_3$ (direct alkylation) and leads to the alkylation of the unsubstituted nitrogen atom in the 5-fluorouracil ring.

Preferably, the unsubstituted nitrogen atom (3-position) in the 5-fluorouracil ring of the derivative is substituted by a halogen substituted precursor under the proviso that the hydroxyl groups present in the 5-fluorouracil derivative are protected by protecting groups. Suitable protecting groups are known to the person skilled in the art. Examples are dimethoxytrityl (DMT) and a tert-butyldimethylsilyl group.

Surprisingly, it has been found that the hydroxyl functional lipophilic precursor (such as the amino alcohols reflected in Scheme 1 and 2) can be selectively reacted with the unsubstituted nitrogen atom of the 5-fluorouracil derivative by a Mitsunobu reaction. This reaction is carried out by first protecting any hydroxyl groups which may be present in the 5-fluorouracil derivative.

The Mitsunobu reaction is generally carried out by reacting the alcohol and the 5-fluorouracil derivative which comprises the unsubstituted ring nitrogen atom in the presence of triphenylphosphine and diisopropylazo dicarboxylate (DIAD).

Further, $R^1$ is preferably a $C_2$ to $C_{40}$ chain which is unsaturated, more preferably a $C_8$ to $C_{28}$ chain which is unsaturated. In one embodiment of the invention $R^1$ comprises one or more carbon-carbon double bond(s) and/or one or more carbon-carbon triple bond(s). In a particular preferred embodiment $R^1$ comprises two or more, especially 2 to 6, such as 2 to 4 carbon-carbon double bonds.

In a specially preferred embodiment the substituents are derived from nature. Suitable naturally derived substituents have a structure derived from terpenes. When terpenes are chemically modified such as by oxidation or rearrangement of the carbon skeleton, the resulting compounds are generally referred to as terpenoids. In a preferred embodiment $R^1$ is a cyclic or alicyclic terpenoid, preferably a terpenoid having 8 to 36 carbon atoms.

The terpenes are preferably selected from monoterpenes, sesquiterpenes, diterpenes, sesterterpenes, triterpenes and sesquaterpenes.

Suitable monoterpenes or monoterpenoids which can be acyclic or cyclic are selected from the group consisting of geraniol, limonene, pinen, bornylen and nerol.

Suitable sesquiterpenes or sesquiterpenoids which can be acyclic or cyclic may inter alia be selected from farnesol.

Suitable sesterterpenes or sesterterpenoids are inter alia selected from geranylfarnesol.

Suitable diterpenes or diterpenoids can be selected from the group consisting of abietic acid, aphidicolin, cafestol, cembrene, ferruginol, forskolin, guanacastepene A, kahweol, labdane, lagochilin, sclarene, stemarene, steviol, taxadiene (precursor of taxol), tiamulin, geranylgeraniol and phytol.

According to an especially preferred embodiment of the invention, $R^1$ is selected from the group consisting of geranyl, farnesyl, seryl and phythyl.

According to a further alternative aspect $R^1$ is H or a $C_3$-$C_{28}$ chain which may be branched or linear and which may be saturated or unsaturated and which may optionally be interrupted and/or substituted by one or more hetero atom(s) (Het1) and/or functional group(s) (G1); or $R^1$ is a $C_1$-$C_{28}$ moiety which comprises at least one cyclic structure and which may be saturated or unsaturated and which may optionally be interrupted and/or substituted by one or more hetero atom(s) (Het1) and functional group(s) (G1);

According to an especially preferred embodiment $R^1$ is selected from H,

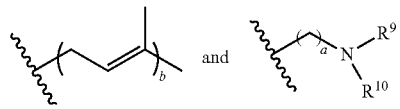

substituted or unsubstituted cyclic terpene moieties, wherein
$R^9$ and $R^{10}$ are independently selected from $C_1$ to $C_{30}$ alkyl,
b is an integer ranging 1 to 4, preferably n is 1 or 2; and
a is an integer ranging from 1 to 20, preferably 2 to 18.

In a further aspect of the invention, group A is a fluorescence marker which is preferably selected from the group consisting of fluorescein isothiocyanate (FITC), phycoerythrin, rhodamide, 2-aminopyridine and coumarine dyes.

In a further aspect of the invention, linker $L^2$ is selected from a single bond or a saturated or unsaturated moiety having 1 to 30, preferably 2 to 20 carbon atoms, more preferably a carbon chain which may be substituted and/or interrupted by one or more functional groups selected from carboxylic acid ester, phosphate ester, carboxylic acid amides, urethane, ether and amine groups. $L^2$ may also comprise cyclic moieties.

According to a preferred embodiment, linker $L^2$ is selected from a single bond; alkandiyl, preferably $C_1$-$C_{20}$-alkandiyl; alkendiyl, preferably a $C_2$-$C_{20}$-alkendiyl; alkyndiyl, preferably a $C_2$-$C_{20}$-alkyndiyl; aryl moiety, aralkyl moiety and heterocyclic moiety.

According to a preferred embodiment linker $L^1$ is selected from a single bond; alkandiyl, preferably $C_1$-$C_{20}$-alkandiyl; alkendiyl, preferably a $C_2$-$C_{20}$-alkendiyl; and alkyndiyl, preferably a $C_2$-$C_{20}$-alkyndiyl;

Preferably, the alkandiyl represents a straight-chain or branched-chain alkandiyl group bound by two different carbon atoms to the molecule, it preferably represents a straight-chain or branched-chain $C_{1-12}$ alkandiyl, particularly preferably represents a straight-chain or branched-chain $C_{1-6}$ alkandiyl; for example, methandiyl (—$CH_2$—), 1,2-ethanediyl (—$CH_2$—$CH_2$—), 1,1-ethanediyl ((—CH($CH_3$)—), 1,1-, 1,2-, 1,3-propanediyl and 1,1-, 1,2-, 1,3-, 1,4-butanediyl, with particular preference given to methandiyl, 1,1-ethanediyl, 1,2-ethanediyl, 1,3-propanediyl, 1,4-butanediyl.

Further, preferably the alkendiyl represents a straight-chain or branched-chain alkendiyl group bound by two different carbon atoms to the molecule, it preferably represents a straight-chain or branched-chain $C_2$-6 alkendiyl; for example, —CH=CH—, —CH=C($CH_3$)—, —CH=CH—$CH_2$—, —C($CH_3$)=CH—$CH_2$—, —CH=C($CH_3$)—$CH_2$—, —CH=CH—C($CH_3$)H—, —CH=CH—

CH=CH—, —C(CH₃)=CH—CH=CH—, —CH=C(CH₃)—CH=CH—, with particular preference given to —CH=CH—CH₂—, —CH=CH—CH=CH—.

The aryl moiety preferably represents an aromatic hydrocarbon group, preferably a C$_{6-10}$ aromatic hydrocarbon group; for example phenyl, naphthyl, especially phenyl which may optionally be substituted. The aromatic moiety may form a linker in that the aromatic moiety is attached to the phosphor acid diester and the group A. The phosphor acid ester group and group A may be in ortho, meta or preferably para-position of the aromatic moiety.

Aralkyl moiety denotes an "Aryl" bound to an "Alkyl" and represents, for example benzyl, α-methylbenzyl, 2-phenylethyl, α,α-dimethylbenzyl, especially benzyl. Aralkyl moiety can be attached to the phosphoracid ester group via the alkyl or via the aryl part of the aralkyl moiety. Likewise group A can be attached to the phosphor acid ester group via the alkyl or via the aryl part of the aralkyl moiety.

Heterocyclic moiety represents a saturated, partly saturated or aromatic ring system containing at least one hetero atom. Preferably, heterocycles consist of 3 to 11 ring atoms of which 1-3 ring atoms are hetero atoms. Heterocycles may be present as a single ring system or as bicyclic or tricyclic ring systems; preferably as single ring system or as benz-annelated ring system. Bicyclic or tricyclic ring systems may be formed by annelation of two or more rings, by a bridging atom, e.g. oxygen, sulfur, nitrogen or by a bridging group, e.g. alkandiyl or alkenediyl. A Heterocycle may be substituted by one or more substituents selected from the group consisting of oxo (=O), halogen, nitro, cyano, alkyl, alkoxy, alkoxyalkyl, alkoxycarbonyl, alkoxycarbonylalkyl, halogenalkyl, aryl, aryloxy, and arylalkyl. Examples of heterocyclic moieties are: pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, furazane (oxadiazole), dioxolane, thiophene, dihydrothiophene, tetrahydrothiophene, oxazole, oxazoline, oxazolidine, isoxazole, isoxazoline, isoxazolidine, thiazole, thiazoline, thiazlolidine, isothiazole, isothiazoline, isothiazolidine, thiadiazole, thiadiazoline, thiadiazolidine, pyridine, piperidine, pyridazine, pyrazine, piperazine, triazine, pyrane, tetrahydropyrane, thiopyrane, tetrahydrothiopyrane, oxazine, thiazine, dioxine, morpholine, purine, pterine, and the corresponding benz-annelated heterocycles, e.g. indole, isoindole, cumarine, cumaronecinoline, isochinoline, cinnoline and the like.

"Heteroatoms" are atoms other than carbon and hydrogen, preferably nitrogen (N), oxygen (O) or sulfur (S).

The heterocyclic moiety may form a linker $L^2$ in that the heterocylic moiety is covalently linked to the phosphor acid ester and the group A.

In a preferred embodiment of the present invention linker L is selected from the group consisting of a single bond and a C$_1$-C$_{10}$ alkandiyl, preferably a C$_2$-C$_6$-alkandiyl, especially ethan-1,2-diyl (ethylene) or propan-1,2-diyl or propan-1,3-diyl.

In an especially preferred embodiment linker $L^2$ is selected from the group consisting of a single bond, a moiety of formula (VII), a moiety of formula (VIII) and a moiety of formula (IX)

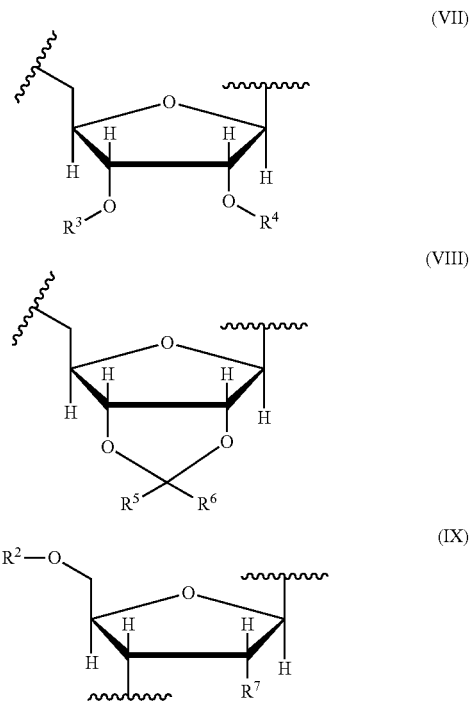

wherein the $R^3$, $R^4$, $R^2$, $R^5$, $R^6$ and $R^7$ are as defined above.

According to an especially preferred embodiment of the invention, X is hydroxyethylstarch and said medicinally active substance A is 5-fluorouracil (5-fluoro-1H-pyrimidine-2,4-dione) or a derivative or a prodrug thereof. Alternatively, substance A may be 5-fluorouridine or a 5-fluorouridine derivative.

An especially preferred embodiment of the invention is represented by the formula (V)

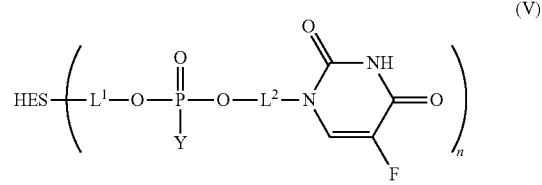

wherein HES is hydroxyethylstarch and $L^1$, $L^2$, Y and n are define as above.

Especially, the organo phosphor forms an ester linkage with the hydroxethyl group of the hydroxyethyl starch. In this case linker $L^1$ in formula (V) is a single bond.

According to a further aspect of the invention the compound of the present invention is represented by the following formula (Ia):

(Ia)

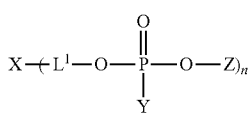

wherein n and Y are defined as above and Z is selected from the group of following moieties with formulae Ib to Ig:

(Ib)

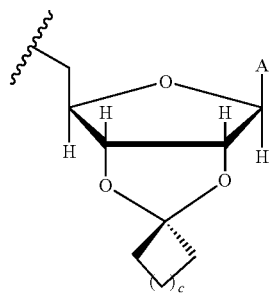

(Ic)

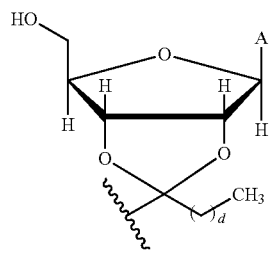

(Id)

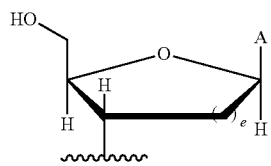

(Ie)

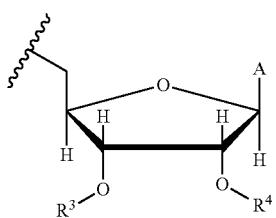

(If)

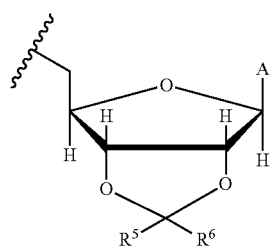

-continued (Ig)

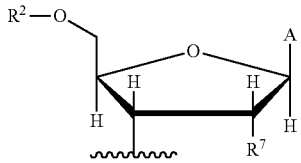

wherein c is an integer ranging from 2 to 12, preferably 3 to 8, more preferably 3 to 6;

d is an integer ranging from 1 to 24, preferably 2 to 18, more preferably 3 to 12;

e is 1 or 2;

$R^3$, $R^4$, $R^2$, $R^5$, $R^6$ and $R^7$ as well as A are as defined above.

A further embodiment of the invention is a pharmaceutical formulation comprising the compound of the invention.

The pharmaceutical formulation is preferably aqueous and injectable.

It has surprisingly been found that the compound of the invention can be obtained by reacting a phosphoramidite, which is linked to a medicinally active substance A or a fluorescence marker A, with a colloid active compound which comprises one or more hydroxyl groups.

The reaction sequence provides an access to pharmaceutically acceptable colloids which are linked with a medicinally active substance or a fluorescence marker and which can be cleaved enzymatically.

Therefore, a further embodiment of the invention is a process for preparing a compound of general formula (I) of the invention by linking a phosphoramidite covalently bonded to a A-$L^2$-group, preferably by linking a compound of formula (VI)

(VI)

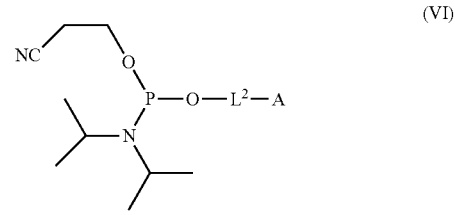

with a compound X-$L^1$-OH or X, which comprise at least one hydroxyl group, wherein X is a colloid active compound, and subsequently oxidizing and hydrolyzing the linked product so as to form a phosphor acid diester. The groups X, A, $L^1$ and $L^2$ are as defined above.

In a preferred embodiment of the invention the colloid active compound X, which is preferably a starch, comprises one or more substituents selected from the group consisting of the moieties reflected in the following formulae:

(Xa)

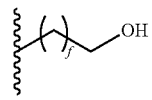

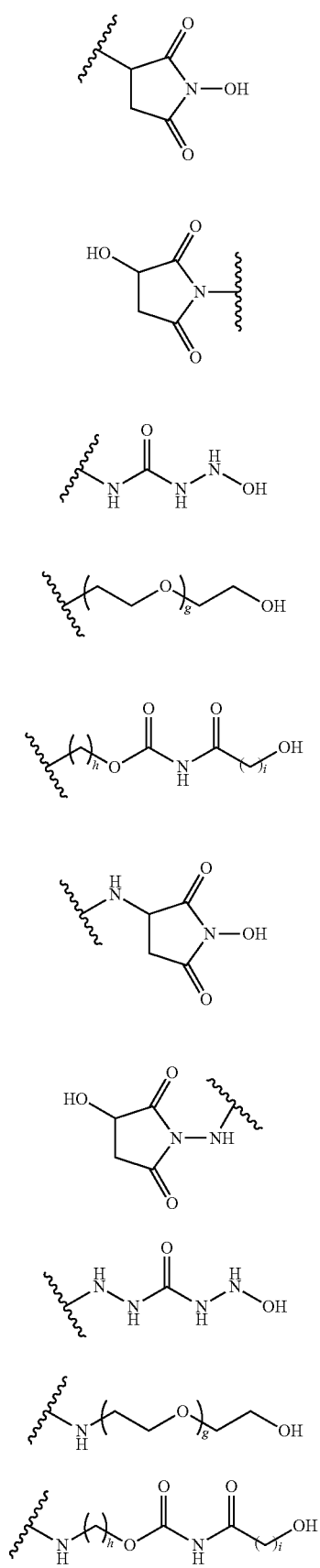
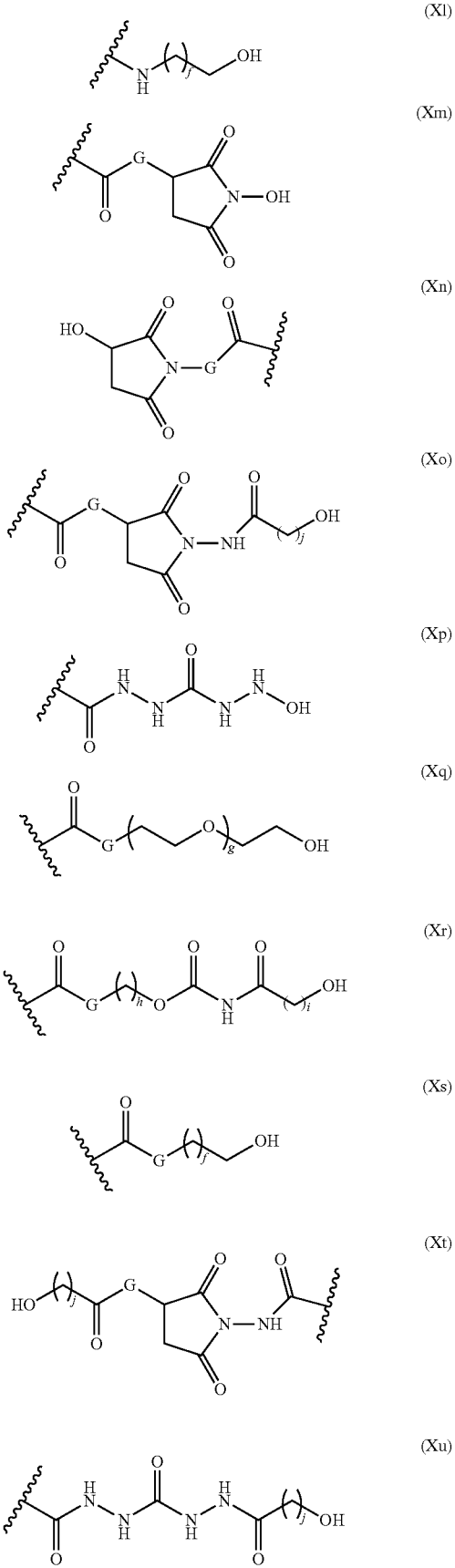

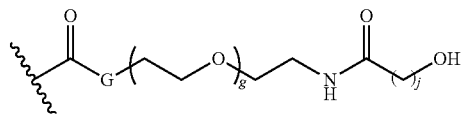

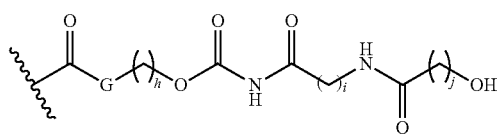

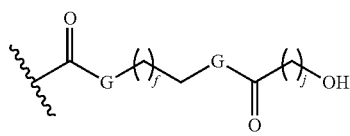

wherein
f is an integer ranging from 1 to 4;
g is an integer ranging from 1 to 10, preferably 1 to 4;
h is an integer ranging from 1 to 4; preferably 2 to 4;
i is an integer ranging from 1 to 4; preferably 2 to 4;
j is an integer ranging from 1 to 4; preferably 2 to 4;
and G is independently selected from —O— or $NR^{11}$, wherein $R^{11}$ is selected from H or $C_1$ to $C_4$ alkyl.

The preparation of phosphoramidites is generally known to the person skilled in the art.

A phosphoramidite $(RO)_2PNR_2$ is a monoamide of a phosphite diester. The key feature of phosphoramidites is their markedly high reactivity towards nucleophiles catalyzed by weak acids e.c., triethylammonium chloride or 1H-tetrazole. In these reactions, the incoming nucleophile replaces the $NR_2$ moiety. Phosphoramidites derived from protected nucleosides are referred to as nucleoside phosphoramidites and are widely used in chemical synthesis of DNA, RNA, and other nucleic acids and their analogs.

Nucleoside phosphoramidites are derivatives of natural or synthetic nucleosides. They are used to synthesize oligonucleotides, relatively short fragments of nucleic acid and their analogs. Nucleoside phosphoramidites were first introduced in 1981 by Beaucage and Caruthers (Beaucage, S. L.; Caruthers M. H. (1981). "Deoxynucleoside phosphoramidites—A new class of key intermediates for deoxypolynucleotide synthesis". Tetrahedron Letters 22: 1859-1862). In order to avoid undesired side reactions, reactive hydroxy and exocyclic amino groups present in natural or synthetic nucleosides are appropriately protected. As long as a nucleoside analog contains at least one hydroxy group, the use of the appropriate protecting strategy allows one to convert that to the respective phosphoramidite and to incorporate the latter into synthetic nucleic acids.

There are three main methods for the preparation of nucleoside phosphoramidites.

The method used most commonly consists in the treatment of a protected nucleoside bearing a single free hydroxy group with phosphorodiamidite under the catalytic action of a weak acid (Nielsen, J.; Marugg, J. E.; Taagaard, M.; Van Boom, J. H.; Dahl, O. (1986). "Polymer-supported synthesis of deoxyoligonucleotides using in situ prepared deoxynucleoside 2-cyanoethyl phosphoramidites". Rec. Trav. Chim. Pays-Bas 105 (1): 33-34; Nielsen, J.; Taagaard, M.; Marugg, J. E.; Van Boom, J. H.; Dahl, O. (1986). "Application of 2-cyanoethyl N,N,N',N'-tetraisopropylphosphorodiamidite for in situ preparation of deoxyribonucleoside phosphoramidites and their use in polymer-supported synthesis of oligodeoxyribonucleotides". Nucl. Acids Res. 14 (18): 7391-7403). 2-cyanoethyl N,N,N',N'-tetraisopropylphosphorodiamidite, the amidite used for the preparation of commercial nucleoside phosphoramidites, is relatively stable. It can be synthesized using a two-step, one-pot procedure and purified by distillation.

According to an alternative method, the protected nucleoside is treated with the phosphorochloridite in the presence of an organic base, most commonly N-ethyl-N,N-diisopropylamine (Hünig's base).

In a further alternative synthetic route for the preparation of phosphoramidites the protected nucleoside is first treated with chloro N,N,N',N'-tetraisopropyl phosphorodiamidite in the presence of an organic base, most commonly N-ethyl-N,N-diisopropylamine (Hünig's base) to form a protected nucleoside diamidite. The latter is treated with an alcohol respective to the desired phosphite protecting group, for instance, 2-cyanoethanol, in the presence of a weak acid. Nucleoside phosphoramidites can be purified by column chromatography on, for example, silica gel. To warrant the stability of the phosphoramidite moiety, it is advisable to equilibrate the column with an eluent containing 3 to 5 wt.-% of triethylamine and maintain this concentration in the eluent throughout the entire course of the separation.

It has surprisingly been found that phosphoramidites can undergo a phosphoramidite coupling reaction with the colloid active compound X which comprises at least one hydroxy group. The reaction can be carried out in the presence of an acidic azole catalyst, 1H-tetrazole, 2-ethylthiotetrazole, 2-benzylthiotetrazole, 4,5-dicyanoimidazole, or a number of similar compounds.

Phosphoramidites are readily oxidized with weak oxidating reagents, for instance, with aqueous iodine in the presence of weak bases or with hydrogen peroxide to form the respective phosphoramidates.

According to a preferred embodiment of the present invention the oxidation step is carried out in the presence of a CSO oxidizer, preferably ((1S)-(+)(10-comphorsulfonyl)-oxaziridine).

The naturally occurring nucleotides (nucleoside-3'- or 5'-phosphates) and their phosphodiester analogs are insufficiently reactive to afford an expedite synthetic preparation of oligonucleotides in high yields. The selectivity and the rate of the formation of internucleosidic linkages are dramatically improved by using 3'-O—(N,N-diisopropyl phosphoramidite) derivatives of nucleosides (nucleoside phosphoramidites) that serve as building blocks in phosphite triester methodology. To prevent undesired side reactions, all other functional groups present in nucleosides should be rendered unreactive (protected) by attaching protecting groups.

Thus, in a preferred embodiment, groups present at group A which may react with the phosphoramidite such as nucleophilic groups, e.g. OH groups are protected by protecting groups which can be cleaved after the coupling reaction with the colloid active compound occurred.

Scheme 3 shows in an exemplary embodiment a synthetic route to obtain a phosphor acid diester attached to a hydroxyethy starch.

Scheme 3

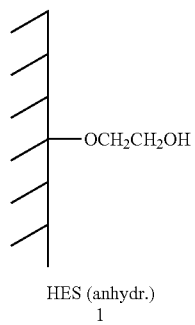

HES (anhydr.)
1

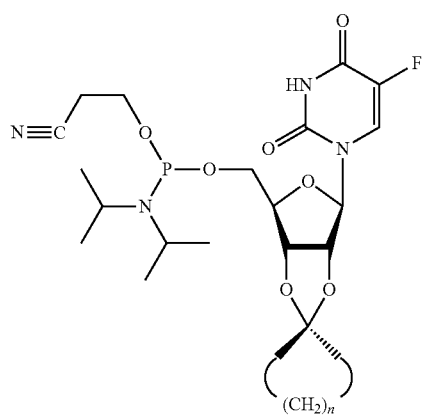

2

(i) MeCN
(ii) I$_2$/H$_2$O
(iii) NH$_3$ aq.

-continued

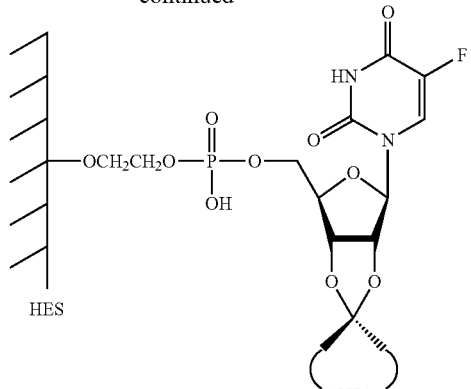

HES

3

In an alternatively preferred embodiment the process according to the invention comprises the following steps:
i) Activation of compound of formula (VI);
ii) Linking the activated compound of step i) with a compound X-L$^1$-OH or X which comprises at least one hydroxyl group;
iii) Oxidizing and hydrolyzing the linked product of step ii) so as to form a phosphor acid diester.

In a preferred embodiment the process according to the invention is carried out as a one-pot reaction. "One-pot reaction" as used herein concerns reactions which are carried out in a single reaction vessel by subsequent addition of the reaction components without isolating any intermediates. Only the final product is isolated from the reaction mixture, for example by means of evaporating the solvent and washing. Thus, it is possible to eliminate several working steps, rendering the reaction more time and economically efficient. Furthermore, the danger of decomposition of the intermediates, for example by accidental exposure to air or water, is minimized.

In a preferred embodiment the compound (VI) in step i) is chemically activated.

In a further preferred embodiment the activation is carried out by an activating agent selected from the group consisting of 4,5-dicyano-imidazole (DCI), saccharine 1-methylimidazole (SMI) and acidic azoles.

In a preferred embodiment the linking reaction of step ii) is carried out for time ranging from 10 to 50 minutes, preferably from 15 to 40 minutes.

Further preferred is an embodiment wherein the reaction temperature is between 15° C. and 40° C., preferably 20° C. to 30° C.

EXAMPLES

It has been found that medicinally active substances or fluorescence marker can be coupled to colloid active compounds comprising at least one hydroxy group, such as hydroxyethyl starch (HES). In Scheme 3 a reaction sequence is shown for a corresponding 5-fluorouridine derivative. For this purpose, 5-fluorouridine is first lipophilized at the O-2',3' position by a cyclic ketal moiety; the ring size is variable. The ketal moiety can be for example obtained by the synthesis disclosed in E. Malecki, H. Rosemeyer, *Helv. Chim. Acta* 2010, 93, 1500. An example is shown in the following formula representing compound 6 wherein n=14.

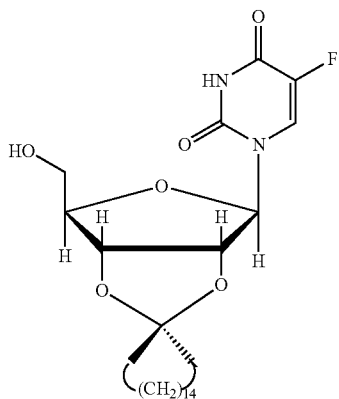

(6)

The ketal moiety further acts as a protecting group. A phosphoramidite 2 with n=14 (hereinafter 2a) can be prepared as follows:

Preparation of Phosporamidite 2a

5-Fluoro-1-[(4'R,6'R)-2',3',4',5'-tetrahydro-6'-(hydroxymethyl)spiro[cyclopentadecane-1,2'-furo[3,4-d][1,3]dioxol]-4'-yl]pyrimidine-2,4(1H,3H)-dione 2-Cyanoethyldiisopropylphosphoramidite (2a)

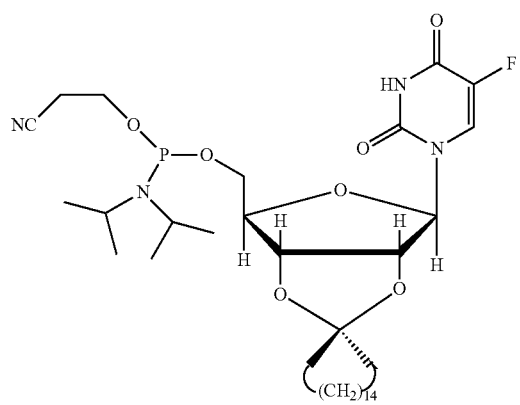

(2a)

Anhydrous compound 6 (256 mg, 0.45 mmol) was 5'-phosphitylated under an nitrogen atmosphere using ethyldiisopropylamine (Hünig's base, 147 µl, 0.85 mmol) and (chloro)(2-cyanoethoxy)(diisopropylamino)phosphine (181 µl, 0.80 mmol) The reaction mixture was stirred for 15 min at room temperature, and then an ice-cold 5% aq. NaHCO₃ solution (12 ml) was added. The mixture was extracted three times with cold CH$_2$Cl$_2$, the combined organic layers were dried (Na$_2$SO$_4$), filtered and evaporated on a rotary evaporator (bath temperature, 25° C.). Chromatography (silica gel, column: 2×8 cm, CH$_2$Cl$_2$/MeOH, 8:2, v/v) gave one main zone from which compound 2a (208 mg, 60%) was obtained as colourless oil. TLC (CH$_2$Cl$_2$/MeOH, 8:2, v/v): R$_f$ 0.95. $^{31}$P-NMR (CDCl$_3$): 149.56, 149.41.

From Scheme 3 it can be seen that the synthesis of the end product 3 implies—after the coupling of the P(III) derivative 2 to HES—the oxidation of 2 with I$_2$/H$_2$O, followed by a cleavage of the cyanoethyl protecting group in concentrate aqueous ammonia. The reactions are preferably performed under strict exclusion of moisture (Ar atmosphere) and using thoroughly dried hydroxyethyl starch (HES). The advantage of a product such as compound 3 is its enzymatic cleavability by phosphodiesterases.

Scheme 4 shows another route for the preparation of a compound of the invention.

Phosphoramidite 4 which is based on 5-(propyn-1-yl)-2'-deoxyuridine a virostatic compound, active against Herpes simplex viruses (A. L. Andronova et al. *Russ. J. Bioorg. Chem.* 2003, 29, 262-266) has been coupled to HES.

Scheme 4

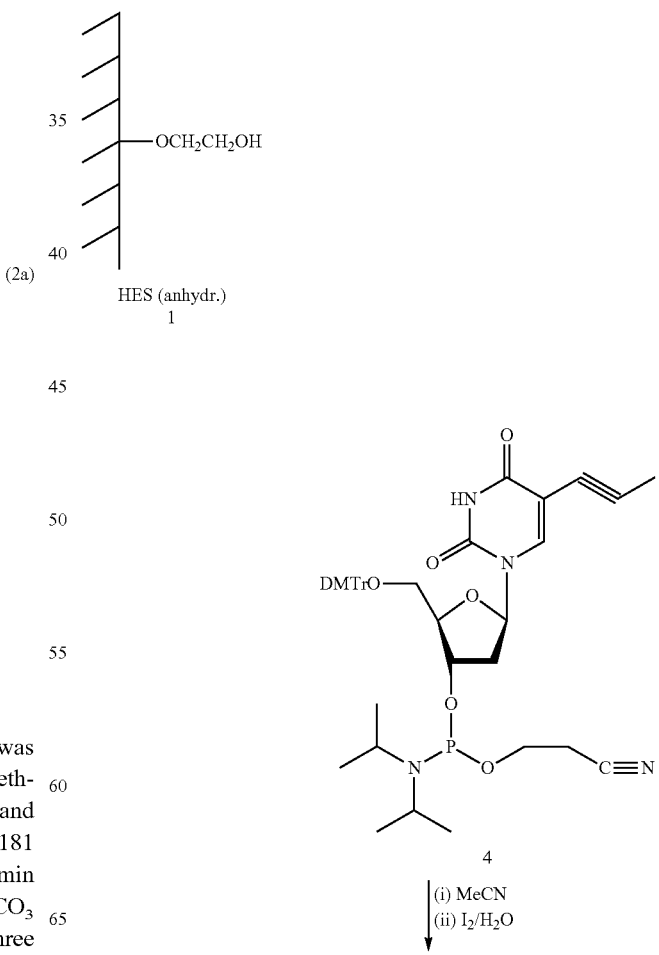

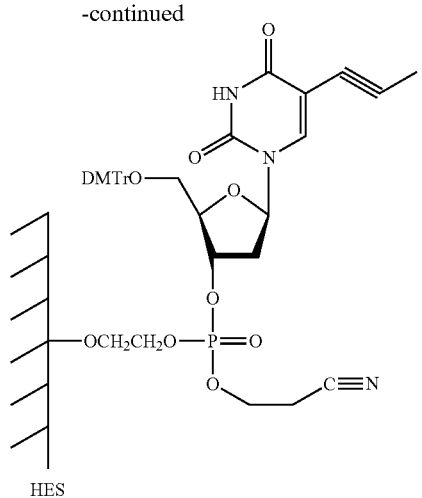

5 one reaction vessel by subsequently adding the respective reaction component without isolation of the intermediates.

In a first step the phosphoramidite (4) and the respective activating agent were mixed together and stirred at ambient temperature under a $N_2$-atmosphere. After 2 hours, hydroxyl ethyl starch (HES) was added and the reaction mixture was stirred for 30 minutes at 20° C. Next, the oxidizing agent was added. Depending on the nature of the oxidizing agent as well as its concentration, the time to completion varied. The respective reaction times are summarized in Table 1. After completion, the solvent was evaporated and the product was purified by washing with MeCN and tetrahydrofurane (THF).

The following activating agents and oxidizing agent were used:

DCI=4,5-dicyano-imidazole
SMI=saccharin 1-methylimididazole
CSO=(1S)-(+)-(10-camphorsulfonyl)-oxaziridine
$I_2$=Iodine

| entry | colloid active compound | activating agent | reaction time [h] | time of coupling [min] | oxidizing agent | reaction time [min] | $^{31}$P-signal of ligand |
|---|---|---|---|---|---|---|---|
| 1 | HES-40 (500 mg) | DCI (0.25 M, 10 ml) | 2 | 30 | $I_2$ (0.02 M, 22 ml) | 1 | + |
| 2 | HES-40 (500 mg) | 1H-tetrazole (0.5 M, 5 ml) | 2 | 30 | $I_2$ (0.02 M, 9 ml) | 7 | + |
| 3 | HES-40 (250 mg) | 1H-tetrazole (0.5 M, 2.5 ml) | 2 | 30 | $I_2$ (0.1 M, 4.5 ml) | 1 | + |
| 4 | HES-40 (250 mg) | 1H-tetrazole (0.5 M, 2.5 ml) | 2 | 30 | $I_2$ (0.02 M, 9 ml) | 1 | + |
| 5 | HES-40 (250 mg) | 1H-tetrazole (0.5 M, 2.5 ml ) | 2 | 30 | $I_2$ (0.02 M, 4.5 ml) | 7 | + |
| 6 | HES-40 (250 mg) | SMI (0.45 M, 5.6 ml) | 2 | 30 | $I_2$ (0.02 M, 4.5 ml) | 7 | + |

HES-40 (1 g) was dried by repeated (7 times) lyophilisation (freeze drying) from anhydrous acetonitrile (MeCN) (20 ml, each) during one week. The HES (500 mg) was transferred into a reactor and purged with anhydrous MeCN (10 ml). Subsequently, the solid was purged with a 0.25 M 4,5-dicyano-imidazole (DCI) activator solution in MeCN (10 ml). Simultaneously, 5-(propin-1-yl)-2'-deoxyuridine 2-(cyanoethyl)(diisopropyl)phosphoramidite (4, 1 g) was dissolved in the DCI activator solution and diluted with MeCN to a total volume of 10 ml. After injection into the reactor, the suspension was slightly agitated for 10 min at room temperature. Then, the product was washed twice with anhydrous MeCN (10 ml, each), and, next, an oxidizer solution (0.02 M $I_2$, THF, pyridine, 10 ml) was injected. After 1 min of agitation within the reactor, the material was washed 4 times with anhydrous MeCN (20 ml, each). For drying, $N_2$ gas was purged through the reactor for several minutes, and the material was removed from the column. $^{31}$P-NMR ($D_6$)DMSO: −1.25 ppm.

In order to optimize the coupling reaction and to determine the ideal reaction conditions different activating agents as well as different oxidizing agents have been employed in the formation of the compound according to the present invention. The results are summarized in Table 1. The outcome of the reaction has been determined by $^{31}$P-NMR spectroscopy.

The reactions were carried out in form of a one-pot reaction, i.e. the entire reaction sequence was carried out in As can be depicted from Table 1, all activating agents employed (DCI, 1H-tetrazole, SMI) were sufficient to activate the phosphoramidite compound and the coupling of the phosphoramidite to HES was successfully carried out.

As can be seen from FIG. 1, which shows the $^{31}$P-NMR spectra of a coupling product of compound (4) to HES, both, DCI as well as 1H-tetrazole, let to the desired coupling product which was detected via $^{31}$P-NMR. Although both activating agent were sufficient the use of 1H-tetrazole lead to fewer side products (spectrum C in comparison to spectrum A wherein DCI was used as activating agent and spectrum B which shows the compound of spectrum A after further purification).

NMR studies of the coupling of compound (4) to HES revealed that the use of 1H-tetrazole as activating agent, without further oxidization, lead to intermediate (6) in which the phosphor is directly bonded to the proton. The proton-coupled $^{31}$P-NMR spectrum shows a split of the main peak into two triplets. The coupling constant was estimated to be around 587 Hz, which indicates a $J^1$(P,H)-coupling. An additional oxidation step leads to diester (7). A possible reaction mechanism is shown in Scheme 5 wherein the moiety "base" represents the 5'-fluorouracil moiety.

Scheme 5

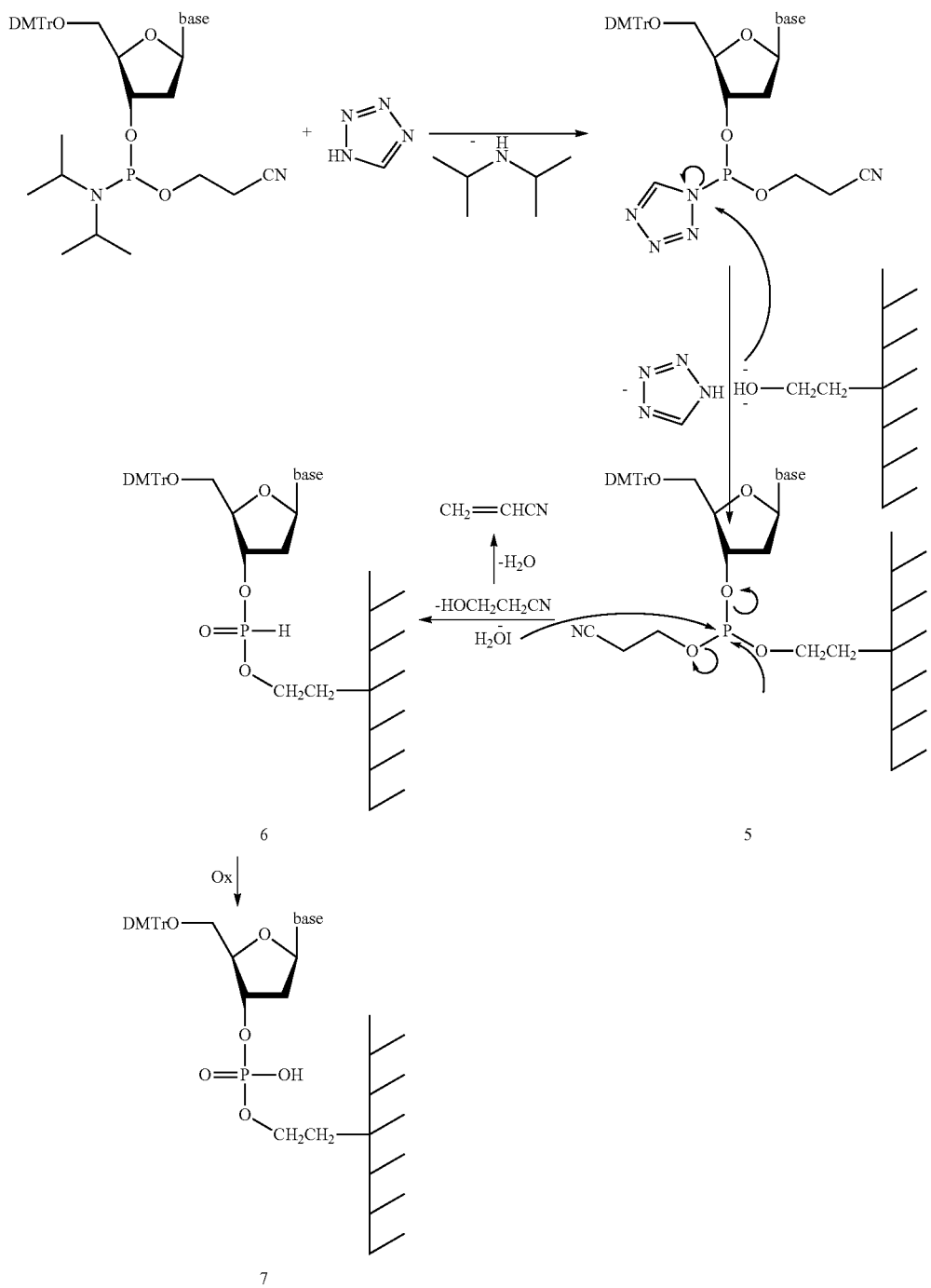

It is believed that, in a first step, the phosphoramidite (4) is activated by 1H-tetrazole, forming a 1H-tetrazole complex which enables the nucleophilic attack of the HES and the formation of a covalent bond. It is believed that the resulting compound (5) in a next step reacts with water that is still present in the HES, leading to intermediate (6) which, after further oxidization, renders the diester (7).

Figure 3:
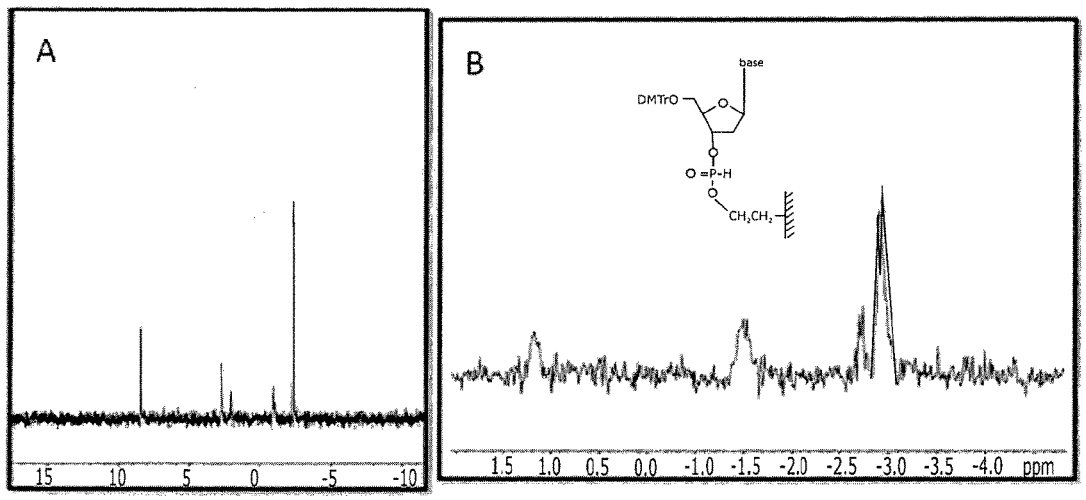

It has surprisingly been found that in cases where SMI was employed as activator, the intermediate (6) could not be detected. FIG. 3 shows the $^{31}$P-NMR spectra of a reaction mixture wherein SMI was used. The proton decoupled recording A shows a new main peak at around −2.4 ppm. The proton coupled spectra B does not show the expected splitting of the main peak. In fact, the coupling constant J was estimated to around 7 Hz which corresponds to a $J^2$(H,P)-coupling, i.e. a coupling of the phosphor atom to the proton of the hydroxyl group of compound (7).

Figure 4:
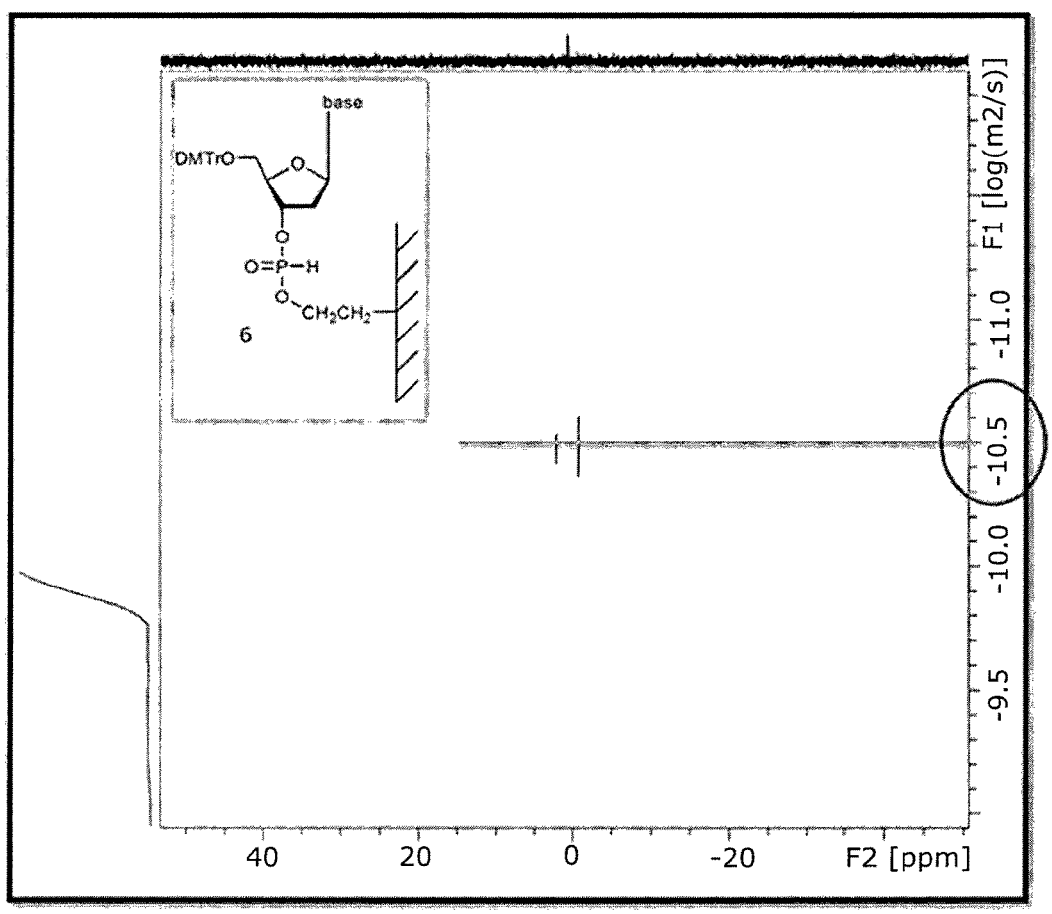

In order to show that the phosphoramidite is covalently bonded to the HES, a proton coupled $^{31}$P-DOSY-NMR spectrum of compound (6) was recorded. FIG. 4 shows the recorded spectrum plotted against the determined diffusion coefficient of compound (6). The coefficient was determined to −10.5 m²/s, which is a typical value for HES as known in the literature. Thus, it can be concluded that the bond between the phosphoramidite moiety and the HES is covalent.

The invention claimed is:
1. A compound of formula (I)

$$X\mathrm{-\!\!\!-\!\!\!(\!L^1\!-\!\!O\!-\!\!\underset{\underset{Y}{\overset{\overset{O}{\|}}{P}}}{\!\!}\!-\!\!O\!-\!\!L^2\!-\!\!A)}_n \quad (I)$$

wherein
X is a colloid-active compound, characterized in that said colloid-active compound X is selected from the group consisting of amyloses, amylopectins, acemannans, arabinogalactans, galactomannans, galactoglucomannans, xanthans, carrageenan, hyaluronic acid, deacetylated hyaluronic acid, starch and modified starch;
$L^1$ is a first linker by means of which X and the phosphate group are covalently linked together and wherein $L^1$ is selected from the group consisting of a single bond, alkandiyl, alkendiyl and alkyndiyl;
$L^2$ is a second linker by means of which the phosphate group and A are covalently linked together;
A is a medicinally active substance selected from the group of consisting of antibiotics, chemotherapeutics, cytostatic agents, antigens, oligonucleotides, mediators, false metabolic substrates, analgetics and cytotoxic substances or a fluorescence marker;
Y is either H or OH;
n is an integer of at least 1.
2. The compound according to claim 1, characterized in that said modified starch is selected from the group consisting of hydroxyalkyl starches, esterified starches, carboxyalkyl starches, hydroxyalkyl carboxyalkyl starch, aminated hydroxyalkyl starch, aminated hydroxyalkyl carboxyalkyl starch and aminated carboxyalkyl starch.
3. The compound according to claim 2, characterized in that said modified starch is selected from hydroxyethyl starch or aminated hydroxyethyl starch.
4. The compound according to claim 1 characterized in that said colloid-active compound has an average molecular weight of from 20,000 to 800,000 daltons.
5. The compound according to claim 1, characterized that the degree of substitution, DS, of the modified starch is from 0.2 to 0.8.
6. The compound according to at least claim 1, characterized in that said medicinally active compound A is selected from formula (II) to (IV)

(II)

(III)

(IV)

wherein
$R^1$ is H or a $C_1$-$C_{28}$ chain which may be branched or linear and which may be saturated or unsaturated and which may optionally be interrupted and/or substituted by one or more hetero atom(s) and/or functional group(s);
or
$R^1$ is a $C_3$-$C_{28}$ moiety which comprises at least one cyclic structure and which may be saturated or unsaturated and which may optionally be interrupted and/or substituted by one or more hetero atom(s) and functional group(s);
$R^2$ is H or an organic moiety comprising 1 to 30 carbon atoms;
$R^3$ and $R^4$ represent independently from each other H or a $C_1$-$C_{28}$-alkyl moiety which may optionally be substituted or interrupted by one or more heteroatom(s) and/or functional group(s); or
$R^3$ and $R^4$ form a ring having at least 5 members, wherein the ring may be substituted or interrupted by one or more hetero atom(s) and/or functional group(s);
$R^5$ and $R^6$ represent independently from each other H or a $C_1$-$C_{28}$-alkyl moiety which may optionally be substituted or interrupted by one or more heteroatom(s) and/or functional group(s);
or
$R^5$ and $R^6$ form a ring having at least 5 members, wherein the ring may be substituted or interrupted by one or more hetero atom(s) and/or functional group(s);
$R^7$ is a hydrogen atom or —O—$R^8$;
$R^8$ is H or $C_1$-$C_{28}$ chain which may be branched or linear and which may be saturated or unsaturated and which may optionally be interrupted and/or substituted by one or more hetero atom(s) and/or functional group(s).
7. The Compound according to claim 6 wherein $R^1$ is selected from H,

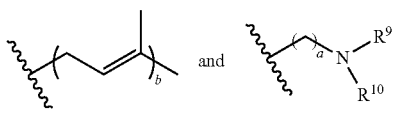 and substituted or unsubstituted cyclic terpene moieties, wherein $R^9$ and $R^{19}$ are independently selected from $C_1$ to $C_{30}$ alkyl, b is an integer ranging 1 to 4; and a is an integer ranging from 1 to 20.

8. The compound according claim 1, characterized in that said fluorescence marker is selected from the group consisting of fluorescein isothiocyanate (FITC), phycoerythrin, rhodamide, 2-aminopyridine and coumarine dyes.

9. The compound according to claim 1, wherein said X is hydroxyethylstarch and said medicinally active substance A is 5-fluorouracil (5-fluoro-1H-pyrimidine-2,4-dione) or a derivative thereof.

10. The compound according to claim 1 which is represented by the formula (V)

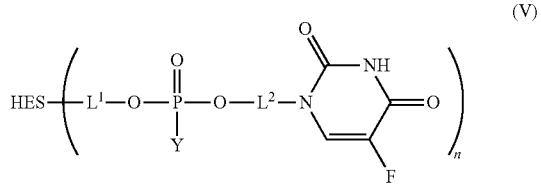

(V)

wherein HES is hydroxyethylstarch.

11. A pharmaceutical formulation comprising the compound according to claim 1.

12. The pharmaceutical formulation according to claim 11, characterized in that said formulation is aqueous and injectable.

13. A process for preparing a compound of general formula (I) according to claim 1 by linking a compound of formula (VI)

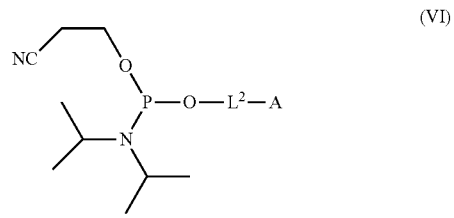

(VI)

with a compound X-$L^1$-OH or X which comprise at least one hydroxyl group, wherein X is a colloid active compound, and subsequently oxidizing and hydrolyzing the linked product so as to form a phosphor acid diester.

14. A process according to claim 13, wherein the process comprises the following steps:

i) Activation of compound of formula (VI), wherein the activation is carried out by an activating agent selected from the group consisting of 4,5-dicyano-imidazole (DCI), saccharin 1-methylimidazole (SMI) and acidic azoles;

ii) Linking the activated compound of step i) with a compound X-$L^1$-OH or X which comprises at least one hydroxyl group;

iii) oxidizing and hydrolyzing the linked product of step ii) so as to form a phosphor acid diester.

15. A process according to claim 13, wherein the process is carried out as a one-pot reaction.

16. A process according to claim 14 wherein the linking reaction of step ii) is carried out for time ranging from 10 to 50 minutes.

17. A process according to claim 13 wherein the reaction temperature is between 15° and 40° C.

* * * * *